United States Patent [19]

Becker et al.

[11] Patent Number: 4,824,674

[45] Date of Patent: Apr. 25, 1989

[54] STABLE ALPHA-INTERFERON DOSAGE FORMS

[75] Inventors: Robert Becker, Biberach; Bernd Kruss, Hochdorf; Leonhard Schilk, Biberach, all of Fed. Rep. of Germany

[73] Assignee: Karl Thomae, Biberach an der Riss, Fed. Rep. of Germany

[21] Appl. No.: 88,187

[22] Filed: Aug. 21, 1987

[30] Foreign Application Priority Data

Aug. 21, 1986 [DE] Fed. Rep. of Germany ....... 3628468

[51] Int. Cl.$^4$ ......................... A61K 9/00; A61K 45/02
[52] U.S. Cl. .................................. 424/427; 424/85.7; 424/422; 427/2
[58] Field of Search ....................... 424/427, 85; 427/2

[56] References Cited

U.S. PATENT DOCUMENTS

| | | | |
|---|---|---|---|
| 3,932,617 | 1/1976 | Nichol, Jr. et al. | 424/85 |
| 4,357,142 | 11/1982 | Schall, Sr. et al. | 427/2 |
| 4,363,634 | 12/1982 | Schall, Jr. | 427/2 |
| 4,414,147 | 11/1983 | Klibanov et al. | 424/85 |
| 4,465,622 | 8/1984 | Nobuhara et al. | 530/351 |
| 4,659,584 | 4/1987 | Schilk | 424/427 |
| 4,680,175 | 7/1987 | Estis et al. | 424/85 |

FOREIGN PATENT DOCUMENTS 2441191  3/1975  Fed. Rep. of Germany.

Primary Examiner—William R. Dixon, Jr.
Assistant Examiner—David M. Brunsman
Attorney, Agent, or Firm—D. E. Frankhouser; Mary-Ellen M. Timbers; Alan R. Stempel

[57] ABSTRACT

Stable, dosage forms of α-interferons, particularly alpha-2-interferon, are described, which comprise a non-lyophilized dry film of acid-stabilized α-interferons, e.g. alpha-2-interferon, on inert carriers.

15 Claims, No Drawings

STABLE ALPHA-INTERFERON DOSAGE FORMS

BACKGROUND OF THE INVENTION

Interferons are proteins with a molecular weight of between 15 and 30 kD, and present great problems of storage owing to their instability. Numerous proposals have been made in the literature for stabilizing interferon-containing preparations, for example using human serum albumin, glucose, mannitol and a number of other compounds as stabilizers. Alpha-interferons have also been proposed for use in the treatment of viral diseases in the eye; however, it is particularly difficult to produce ointments or drops which will retain their activity for shelf storage.

Japanese Kokai Tokyo Koho J. P. No. 55/102519 (80 102.519) describes a method of stabilizing interferon by freeze-drying in the presence of Tris(hydroxymethylamino)-methane, a non-ionic polyethylene surfactant and an antibiotic. It was reported in U.S. Pat. No. 4,252,791 that lanthanides and calcium salts increase the mechanical and thermal stability of interferons. It is known from European Patent Application No. 82.481 that amino acids (e.g. glycine and alanine) stabilize buffered (pH 7.0–7.4) lyophilized interferon. According to Sedmak, J.J., et. al. (Adv. Exp. Med. Biol. 1978, 110), human fibroblast interferon at low pH values is only stable in the presence of more than 5 mcg/ml of protein, and mechanical stress has an inactivating effect on the interferon. It can be said that interferons in general, and alpha-2-interferon in particular, very rapidly lose their activity in aqueous solution without any stabilizers and even pure interferon lyophilizates prepared by freeze-drying acidic aqueous solutions are only relatively stable on storage if stabilizers such as human serum albumin and optionally buffer substances such as ammonium acetate buffer are added to them.

THE INVENTION

This invention relates to new forms for application of $\alpha$-interferons, and particularly alpha-2interferon, comprising a non-lyophilized, dry film of acid-stabilized $\alpha$-interferons, e.g. alpha-2-interferon, on an inert carrier such as glass or inert plastic, the carrier preferably comprising
   (a) eye rods having even amounts of $\alpha$-interferons applied to their ends, for ophthalmological use for inserting the active substance into the conjunctival sac or
   (b) an ampoule having a film of $\alpha$-interferons adhering to its inner walls, for the preparation of injectable solutions.

The eye rods which are addressdd here for ophthalmological use are the subject of W. Ger. Pat. No. 2 441 191. These eye rods make it possible to apply active substances, conventionally used in ophthamology such as fluorescein and metopiolol, between the lower eyelid and the eyeball in the correct dosage. These eye rods provide an accurate dosage, and, unlike eye drops, cause no irritation to the eye. In employing such rods, the end of the rod with dose of medicament is placed above the lower eyelid and the rod is rotated two or three times; this should release all the active substance.

It has now been found that non-lyophilized dry films comprising protonated $\alpha$-interferons, particularly alpha-2-interferon, supported by inert surfaces, e.g. glass or plastics, have exceptionally good storage qualities. The non-lyophilized dry films are produced by quantitatively dissolving the $\alpha$-interferon in an acidic, strongly polar solvent at a pH of between 1.5 and 5, preferably between 3 and 4, applying the solution to an inert carrier of glass or plastic (e.g. polystyrene, polyethylene, polypropylene, polycarbonate) and removing the solvent at temperatures of between 0° C. and 80° C., preferably at ambient temperature. Suitable solvents include water, aliphatic alcohols with 1 to 4 carbon atoms, aliphatic ketones with 3 to 5 carbon atoms or mixtures of these solvents. Examples of acids which may be used to adjust the pH value include inorganic acids such as sulphuric or phosphoric acid and particularly hydrochloric acid, whilst examples of organic acids include fumaric, tartaric, succinic and citric acid.

It is particularly advantageous if the $\alpha$-interferon is dissolved in an azeotropically distillable mixture of water and an alcohol, such as methanol or ethanol, to which an acid, preferably hydrochloric acid, has previously been added in order to adjust the pH to the desired value, since after application of this solution to the carrier in question every last trace of the water present can easily be removed. Since the $\alpha$-interferons are most soluble in acidic aqueous solutions, it is advisable to add sufficient alcohol to an aqueous solution thus prepared to ensure that the water present can be removed completely together with the alcohol as an azeotropic mixture at room temperature under reduced pressure. The storage stability of the film formed on the carrier is greater the lower the moisture content of the film.

Before the coating is carried out it is advisable to sterilize the carrier material and also to sterilize by filtration the active substance solution. However, as an additional step, it is also possible to sterilize the coated product by subsequent irradiation (e.g. with $\beta$- or $\gamma$-rays).

Surprisingly, a dry film of a protonated $\alpha$-interferon thus obtained retains its activity almost unimpaired even when stored for several months at ambient temperature (and even when kept at 60° C. for 5 days the active substance still shows nearly 90% of its original activity), whereas a film of the same material loses 10% of its initial activity just through freeze-drying. Even the presence of residual traces of moisture does not affect the stability of the active substance, due to protonation of the interferon.

Another surprising fact is that the film of active substance obtained according to the invention is easily detached mechanically, which is very important for medication used on the eye, and it dissolves very rapidly in water, better still in, for example, a 0.1N hydrochloric acid solution, and particularly well in tears. The interferon film of the present invention is therefore, particularly suitable for coating eye rods.

No special cooling equipment is required for the practice of the present invention nor are any additives required, such as stabilizers, which had been assumed to be essential in the preparation of pharmaceutical forms of interferon with a long shelf life.

The forms for application of $\alpha$-interferons, particularly alpha-2-interferon, suitable for ophthalmology consist of so-called eye rods (cf. Ger. Pat. No. 2 441 191) in which one or both ends of these rods are coated with an acidic, aqueous, aqueous-alcoholic solution or an acidic, preferably water-containing, dialkyl ketone, e.g. acetone solution containing $\alpha$-interferon, the solvent then immediately eliminated until a dry film is formed.

The solutions used on the eye rods contain α-interferon in a concentration generally ranging from 0.025 to 2 mg/ml, preferably from 0.5 to 1.5 mg/ml. The quantity of α-interferon applied to each eye rod is between 0.5 and 50 mcg, preferably 5 to 20 mcg (mcg = microgram).

The α-interferon, e.g. recombinant alpha-2interferon, which occurs in powder form in its pure state, is taken up in an acidic buffer solution (e.g. in an HCl-glycine buffer solution), but preferably in water or in a weak hydrochloric acid solution, e.g. in 0.001 to 0.1N hydrochloric acid, until a clear solution is obtained. The solution is then adjusted to the desired concentration, e.g. by the addition of ethanol, to give an interferon concentration of for example 0.5 mg/ml and an ethanol concentration of 20 to 90%, preferably 70% (v/v). A system-specific pH of generally from 1.5 to 4.5 is measured. In order to improve the adhesion of the resulting solution to the eye rods, a matrix may also be added in a quantity of from 0.05 to 2% by weight, whilst the matrix which improves the adhesion to the eye rods may consist of substances such as polyvinyl alcohol, polyvinylpyrrolidone or celluloses such as methyl cellulose, hydroxypropylmethyl cellulose, carboxymethyl cellulose, hydroxyethyl cellulose, high molecular solid polyethylene glycols or mixtures of these substances. However, it is also possible to use other matrices provided that the interferons are stable therein and provided that these matrices are readily soluble in liquids and well tolerated by the eye. In the case of some carrier materials there is no need for a matrix to be added at all; the nature of the surface of the carrier materials will determine whether such additions are desirable or not. As already mentioned, the matrix acts as an adhesive, but it may also simultaneously have a favourable effect on the mechanical stability of the film and it may also be used to help regulate the viscosity of the charging solution. In order to shorten the drying times, it is advantageous to start with the highest possible concentrations of the volatile solvent.

Application to specific zones of the eye rods may be carried out using methods described in W. Ger. Pat. No. 2 441 191, e.g. by dipping the ends of the eye rods, in controlled manner, into a solution according to the invention which contains an interferon. The dipping process, however, will result in a not inconsiderable waste of expensive active substance. It is therefore desirable to dot the solution of active substance onto the zones of the eye rods which will be in contact with the conjunctival sac using the method described in W. Ger. Pat. Appln. P No. 35 13 288.4, whilst at the same time or subsequently evaporating off the solvent. The solvent is preferably removed by directing a warm current (40° to 80° C.) of sterile gas, e.g. air, over the zones of the eye rods to which the α-interferon solution has been applied.

In order to prepare ampoules containing α-interferon, the acid solution containing interferon is sterilized by filtration and then Poured into suitable sterile containers made of plastic or glass. The solvent is slowly eliminated at room temperature or at temperatures of up to 50° C. under reduced pressure; thus, for example, after the containers have been filled they are cooled by slow evacuation and then slowly brought to room temperature under vacuum until all the solvent has been removed, but preferably low temperature distillation is used, whilst avoiding freezing of the solution. The containers, e.g. ampoules, coated in this way are then sealed, e.g. by fusion of the glass neck. Before administration, the contents of the dry ampoule are dissolved in a sterile isotonic solution.

In the prior art methods of stabilizing alpha-2-interferon preparations, so-called stabilizers were used; a preferred stabilizer was human serum albumin (HSA). Even if freeze drying is replaced by the drying method according to the invention, poorer storage qualities are obtained with such stabilizers than without them. This is clear from the following observations:

ROD A

An acid solution of alpha-2-interferon prepared from 5 mg of alpha-2-interferon dissolved in 3 ml of 0.003N hydrochloric acid together with 10 mg of HSA and 25 mg of methocel was combined with 7 ml of ethanol (pH of the solution 3.6), sterilized by filtration and dotted onto one end of an eye rod whilst the solvent was simultaneously eliminated by passing a sterile air current at 60° C. over the eye rod. 10 mcl of the charging solution were dotted onto each eye rod, each rod therefore carried 5 mcg of alpha-2-interferon.

ROD B

An acidic solution of alpha-2-interferon according to the invention, prepared from 5 mg of alpha-2-interferon dissolved in 3 ml of 0.0015N hydrochloric acid and mixed with 7 ml of ethanol (pH value of the charging solution 4.2) was applied to the ends of the eye rods analogously. Once again, each eye rod carried a quantity of 5 mcg of alPha-2-interferon.

Eye rods A and B were subjected to a comparative investigation of their storage qualities, first through storage for 48 hours at 60° C. and second by storage for one month at 41° C. In this way, the activity of the stored active substance was determined (ELISA test method) and expressed in % based on the initial activity (=100%). The following Table contains the values found:

|  | Activity of the active substance after a storage time and temperature of | |
|---|---|---|
|  | 48 hours/60° C. | 1 month/41° C. |
| Eye rod A | 81.4% | 69.8% |
| Eye rod B | 94.0% | 84.0% |

The stabilizer-free forms for application according to the present invention are thus significantly more stable on storage than corresponding forms stabilized with additives. As already described, the activities of the active substance in freeze-dried forms are substantially lower (cf. page 4).

The Examples which follow serye to illustrate the invention more fully (mcg=microgram, mcl =microliter):

EXAMPLE 1

Eye rod 50 mg of powdered recombinant alpha-2-interferon were taken up in 10 ml of 0.01N hydrochloric acid and the solution was mixed with 90 ml of pure ethanol. 0.5 g of Hydroxypropylmethyl cellulose is added to this solution. The resulting solution (pH 3.5) was sterilized by filtration and 10 mcl were applied to one end of a sterile eye rod and simultaneously dried in a current of sterile air at 60° C.

The quantity of solution applied to each eye rod contains 5 mcg of alpha-2-interferon.

The eye rods were stored for 5 days at 60° C. and then the content of active substance was determined as 85%, based on the initial value.

Analogously, in Examples 2 to 6 which follow, eye rods were treated with an acidic solution of alpha-2-interferon having the following composition:

| Substance | Quantity | Examples | | | | |
|---|---|---|---|---|---|---|
| | | 2 | 3 | 4 | 5 | 6 |
| Alpha-2-interferon | mg/ml | 0.5 | 0.5 | 1.5 | 1.0 | 1.5 |
| Methanol | % v/v | — | — | — | 50 | — |
| Ethanol | % v/v | 70 | 90 | 70 | — | 70 |
| Hydrochloric acid | ad pH | 3.5 | 3.0 | 4.2 | 4.0 | 3.5 |
| Methyl cellulose | % by wt. | — | — | — | 0.2 | — |
| Polyvinyl alcohol | % by wt. | — | — | — | — | 2 |

The charging volume for each eye rod, treated at one end, was 10 mcl in Examples 2 to 6. The eye rods consisted of glass and polystyrene.

EXAMPLE 7

Dry ampoules containing alpha-2-interferon 20 mg of powdered recombinant alpha-2-interferon were taken up in 4 ml of 0.1N hydrochloric acid, the solution was combined with 36 ml of pure ethanol, pH of the solution 2.7. The solution thus obtained was sterilized by filtration; from this solution, 40 mcl were transferred into a sterilized glass ampoule. Content of active substance per ampoule: 20 mcg. The ampoules were then slowly cooled by the application of a vacuum, the residual quantities of solvent were eliminated after heating the ampoules to room temperature or temperatures of up to 40° C. in vacuo. The ampoules containing dry film were sealed to make them airtight.

Analogously, in Examples 8 to 11 which follow, ampoules were charged with 30 mcl of an acidic solution of alpha-2-interferon having the following composition:

| Substance | Quantity | Examples | | | |
|---|---|---|---|---|---|
| | | 8 | 9 | 10 | 11 |
| Alpha-2-interferon | mg/ml | 0.5 | 1.0 | 1.0 | 0.5 |
| Ethanol | % v/v | 70 | — | 50 | — |
| Methanol | % v/v | — | 85 | — | — |
| Hydrochloric acid | ad pH | 3.0 | 2.5 | — | 3.5 |
| Sulphuric acid | ad pH | — | — | 3.8 | — |

In Example 11, water alone was used as solvent.

EXAMPLE 12

| Eye rods Recipe for the composition used for each eye rod: | |
|---|---|
| Alpha 2-interferon | 5 mcg |
| Polyvinylpyrrolidone | 25 mcg |
| Citric acid x H₂O | 2.5 mcg |
| H₂O/Ethanol (70% v/v) ad | 10 mcl |

Preparation of the solution and treatment of the eye rods were carried out as described in Example 1.

EXAMPLE 13

| Eye rods Recipe for the composition used for each eye rod: | |
|---|---|
| Alpha-2-interferon | 8 mcg |
| Hydroxypropylmethylcellulose | 10 mcg |
| 0.001 N hydrochloric acid/ethanol (50%, v/v) ad | 10 mcl |

Preparation of the solution and treatment of the eye rods were carried out as described in Example 1.

EXAMPLE 14

| Eye rods Recipe for the composition used for each eye rod: | |
|---|---|
| Alpha-2-interferon | 10 mcg |
| Polyvinyl alcohol | 50 mcg |
| 0.01 N hydrochloric acid/ethanol (70%, v/v) ad | 10 mcl |

Preparation of the solution and treatment of the eye rods were carried out as described in Example 1.

What is claimed is:

1. Alpha-interferon dosage form comprising a non-lyophilized dry film of acid-stabilized $\alpha$-interferon, and an inert carrier supporting said film.

2. The dosage form as recited in claim 1 further characterized in that the inert carrier is a glass or plastic rod which supports the film on an end thereof.

3. The dosage form as recited in claim 1 further characterized in that the inert carrier is a plastic or glass ampoule which supports the film on an inner wall.

4. The dosage form as recited in claim 1 further characterized in that the $\alpha$-interferon is alpha-2-interferon.

5. The dosage form as recited in claim 1 further comprising a matrix which promotes adhesion by the film to the inert carrier.

6. The dosage form as recited in claim 1 further characterized in that the film contains 0.5 to 50 micrograms of $\alpha$-interferon.

7. The dosage form as recited in claim 5 further characterized in that the matrix which promotes adhesion comprises polyvinyl alcohol, polyvinylpyrrolidone, high molecular solid polyethylene glycols or celluloses such as methyl cellulose, hydroxypropylmethyl cellulose, hydroxyethyl cellulose, carboxymethyl cellulose, or mixtures of these substances.

8. A method of preparing stable, dry $\alpha$-interferons which comprises dissolving an $\alpha$-interferon in an, strongly polar solvent with an added acid at a pH of between 1 and 5, applying the solution to an inert carrier, and removing the solvent at temperatures between 0° and 80° C.

9. The method as recited in claim 8 further comprising sterilizing by filtration the solution of $\alpha$-interferon before applying said solution to the inert carrier.

10. The method as recited in claim 8 wherein the strongly polar solvent comprises water, an aliphatic alcohol with 1 to 4 caron atoms, an aliphatic ketone with 3 to 5 carbon atoms or a mixture of these components and the ratios by volume of any of these components in an aqueous mixture are selected so that they can be distilled off as azeotropic mixtures.

11. The method as recited in claim 8 wherein the acid comprises sulphonic, phosphoric or hydrochloric acid, fumaric, tartaric, succinic or citric acid and the solvent has a pH of 2 to 4.

12. The method as recited in claim 8 wherein the inert carrier is a plastic or glass rod and the solution is applied to one or both ends of such rod.

13. The method as recited in claim 8 wherein the inert carrier is a plastic or glass ampoule and the solution is applied to the inner wall of such ampoule.

14. A method of preparing stable, dry $\alpha$-interferon which comprises dissolving an $\alpha$-interferon in an acidic, strongly polar solvent at a pH of between 1 and 5, sterilizing such solution by filtration, applying the solution to a sterile, inert carrier, and removing the solvent at temperatures between 0° and 80° C.

15. A method of preparing stable, dry $\alpha$-interferons which comprises dissolving an $\alpha$-interferon in an acidic, strongly polar solvent at a pH of between 1 and 5, applying the solution to an inert carrier, removing the solvent at temperatures between 0° and 80° C., and sterilizing the film and carrier.

* * * * *